US00PP23451P2

(12) United States Plant Patent
Saul

(10) Patent No.: US PP23,451 P2
(45) Date of Patent: Mar. 5, 2013

(54) *ALTERNANTHERA* PLANT NAMED 'MIMOSA'

(50) Latin Name: *Alternanthera ficoidea*
Varietal Denomination: Mimosa

(75) Inventor: Robert Mark Saul, Atlanta, GA (US)

(73) Assignee: Itsaul Plants LLC, Alpharetta, GA (US)

( * ) Notice: Subject to any disclaimer, the term of this patent is extended or adjusted under 35 U.S.C. 154(b) by 0 days.

(21) Appl. No.: 13/506,269

(22) Filed: Apr. 7, 2012

(51) Int. Cl.
*A01H 5/00* (2006.01)

(52) U.S. Cl. ..... Plt./373; Plt./263.1
(58) Field of Classification Search ..... Plt./373, Plt./263.1
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Alternanthera* plant named 'Mimosa', characterized by its overall rounded plant habit with lateral branches upright to outwardly spreading and trailing; freely branching habit; dense and bushy growth habit; strong and healthy leaves; leaves that are dark green in color with random sectors of varying shades of pink and red purple; and good garden performance.

2 Drawing Sheets

Botanical designation: *Alternanthera ficoidea.*
Cultivar denomination: 'MIMOSA'.

BACKGROUND OF THE INVENTION

The present invention relates to a new and distinct cultivar of *Alternanthera* plant, botanically known as *Alternanthera ficoidea* and hereinafter referred to by the name 'Mimosa'.

The new *Alternanthera* plant is a naturally-occurring branch mutation of *Alternanthera ficoidea* 'Partytime', disclosed in U.S. Plant Pat. No. 14,789. The new *Alternanthera* plant was discovered and selected by the Inventor from within a population of plants of 'Partytime' in a controlled greenhouse environment in Alpharetta, Ga. during the summer of 2008.

Asexual reproduction of the new *Alternanthera* plant by vegetative cuttings in a controlled greenhouse environment in Alpharetta, Ga. since July, 2008 has shown that the unique features of this new *Alternanthera* plant are stable and reproduced true to type in successive generations.

SUMMARY OF THE INVENTION

Plants of the new *Alternanthera* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Mimosa'. These characteristics in combination distinguish 'Mimosa' as a new and distinct *Alternanthera* plant:

1. Overall rounded plant habit with lateral branches upright to outwardly spreading and trailing.
2. Freely branching habit; dense and bushy growth habit.
3. Strong and healthy leaves.
4. Leaves that are dark green in color with random sectors of varying shades of pink and red purple.
5. Good garden performance.

Plants of the new *Alternanthera* differ primarily from plants of the parent, 'Partytime', in leaf color as plants of 'Partytime' have leaves green, creamy white and red purple-colored leaves. In addition, plants of the new *Alternanthera* have smaller leaves than plants of 'Partytime'.

Plants of the new *Alternanthera* can be compared to plants of *Alternanthera ficoidea* 'Creme de Menthe', disclosed in U.S. Plant Pat. No. 16,263. In side-by-side comparisons conducted in Alpharetta, Ga., plants of the new *Alternanthera* differed from plants of 'Creme de Menthe' in the following characteristics:

1. Plants of the new *Alternanthera* were not as upright as plants of 'Creme de Menthe'.
2. Plants of the new *Alternanthera* and 'Creme de Menthe' differed in leaf color as plants of 'Creme de Menthe' had green and pale yellow-colored leaves.

Plants of the new *Alternanthera* can also be compared to plants of *Alternanthera ficoidea* 'Raspberry Rum', disclosed in U.S. Plant Pat. No. 21,016. In side-by-side comparisons conducted in Alpharetta, Ga., plants of the new *Alternanthera* differed from plants of 'Raspberry Rum' in the following characteristics:

1. Plants of the new *Alternanthera* were not as upright as plants of 'Raspberry Rum'.
2. Plants of the new *Alternanthera* and 'Raspberry Rum' differed in leaf color as plants of 'Raspberry Rum' had hot pink and brown-colored leaves.

BRIEF DESCRIPTION OF THE PHOTOGRAPHS

The accompanying colored photographs illustrate the overall appearance of the new *Alternanthera* plant showing the colors as true as it is reasonably possible to obtain in colored reproductions of this type. Colors in the photographs may differ slightly from the color values cited in the detailed botanical description which accurately describe the colors of the new *Alternanthera* plant.

The photograph on the first sheet comprises a side perspective view of a typical flowering plant of 'Mimosa' grown in a container.

The photograph on the second sheet is a close-up view of a typical flowering plant of 'Mimosa'.

DETAILED BOTANICAL DESCRIPTION

The aforementioned photographs and following observations, measurements and values describe plants grown during the late winter and early spring in one-gallon containers in a polyethylene-covered greenhouse in Alpharetta, Ga. During the production of the plants, day temperatures ranged from 10° C. to 38° C. and night temperatures ranged from 10° C. to 24° C. Plants were two years old when the photographs and detailed description were taken. In the following description, color references are made to The Royal Horticultural Society Colour Chart, 2007 Edition, except where general terms of ordinary dictionary significance are used.

Botanical classification: *Alternanthera ficoidea* 'Mimosa'.

Parentage: Naturally-occurring branch mutation of *Alternanthera ficoidea* 'Partytime', disclosed in U.S. Plant Pat. No. 14,789.

Propagation:

*Type*.—By vegetative cuttings.

*Time to initiate roots, summer*.—About ten days at 24° C. to 27° C.

*Time to initiate roots, winter*.—About two weeks at 21° C. to 24° C.

*Time to produce a rooted young plant, summer*.—About four weeks at 24° C. to 27° C.

*Time to produce a rooted young plant, winter*.—About 38 to 42 days at 21° C. to 24° C.

*Root description*.—Fine, fibrous; white in color.

*Rooting habit*.—Freely branching; medium density.

Plant description:

*Plant form and growth habit*.—Herbaceous subshrub; overall rounded plant habit; lateral branches upright to outwardly spreading and trailing; freely branching and densely foliated, bushy appearance; moderately vigorous growth rate.

*Branching habit*.—Freely basal branching habit with lateral branches potentially forming at every node.

*Plant height*.—About 43 cm.

*Plant diameter*.—About 55 cm.

*Lateral branch description*.—Length: About 40 cm. Diameter: About 5 mm. Internode length: About 4.4 cm. Strength: Strong; flexible. Texture: Smooth, glabrous. Color, developing: Close to N137A to N137B or 59C. Color, developed: Close to N137A to N137B overlain with varying degrees of between 59C and 60C or close to between 59C and 60C.

*Leaf description*.—Arrangement: Opposite; simple; strong and healthy leaves. Length: About 6.2 cm. Width: About 4.1 cm. Shape: Ovate. Apex: Acuminate. Base: Obtuse with cuneate tendencies. Margin: Entire. Texture, upper and lower surfaces: Smooth, glabrous; rugose. Venation: Pinnate. Color: Developing leaves, upper surface: Close to N137A to N137B with or without random sectors of N57A, 58A, 52A to 52B, or 63A to 63B. Developing leaves, lower surface: Close to 146A with or without random sectors of dulled N57A, dulled 58A, dulled 52B, or dulled 63A to 63B. Fully expanded leaves, upper surface: Close to N137A with or without random sectors of 63A to 63B, N57A, 58A or 52B; midvein, close to N137A to N137B or 59A; lateral veins, similar to leaf surface color(s). Fully expanded leaves, lower surface: Close to 146A with or without random sectors of dulled 63A to 63B, dulled N57A, dulled 58A or dulled 52B; midvein, close to 146B or 59A; lateral veins, similar to leaf surface color(s). Petiole: Length: About 2.7 cm. Diameter: About 2 mm. Texture, upper and lower surface: Smooth, glabrous. Color, upper and lower surfaces: Close to 59A to 59C or 60C.

Flower description:

*Flower arrangement and habit*.—Small single funnel-form flowers arranged on branched terminal and upper axillary racemes; freely flowering habit with numerous flowers developing per inflorescence; flowers face outwardly.

*Fragrance*.—None detected.

*Natural flowering season*.—Long flowering period, plants flower repeatedly from spring to autumn.

*Inflorescence length*.—About 17 cm.

*Inflorescence width*.—About 10.5 cm.

*Flower diameter*.—About 1 mm.

*Flower length*.—About 1.5 mm.

*Flower buds*.—Length: About 3 mm. Diameter: About 2 mm. Shape: Oblong. Color: Close to N137B.

*Petals*.—None observed.

*Sepals*.—Quantity: Five sepals fused into a narrow tube; apices free. Length: Less than 1 mm. Width: Less than 1 mm. Lobe shape: Rounded. Apex: Obtuse. Margin: Entire. Texture, upper and lower surfaces: Smooth, glabrous. Color: When opening, inner and outer surfaces: Close to 154D. Fully opened, inner and outer surfaces: Close to 155A.

*Peduncles*.—Length: About 17 cm. Diameter, at the base: About 2.5 mm. Strength: Strong, flexible. Aspect: Mostly outwardly. Texture: Smooth, glabrous. Color: Close to N137A to N137B.

*Pedicels*.—Length: Less than 1 mm. Diameter: Less than 1 mm. Strength: Strong, flexible. Aspect: Mostly outwardly. Texture: Smooth, glabrous. Color: Close to 146A.

*Reproductive organs*.—None observed.

*Seeds and fruits*.—Seed and fruit development have not been observed on plants of the new *Alternanthera*.

Disease & pest resistance: Plants of the new *Alternanthera* have not been observed to be resistant to pathogens and pests common to *Alternanthera* plants.

Garden performance: Plants of the new *Alternanthera* have been observed to have good garden performance and tolerate rain, wind and temperatures ranging from about 2° C. to about 38° C.

It is claimed:

1. A new and distinct *Alternanthera* plant named 'Mimosa' as illustrated and described.

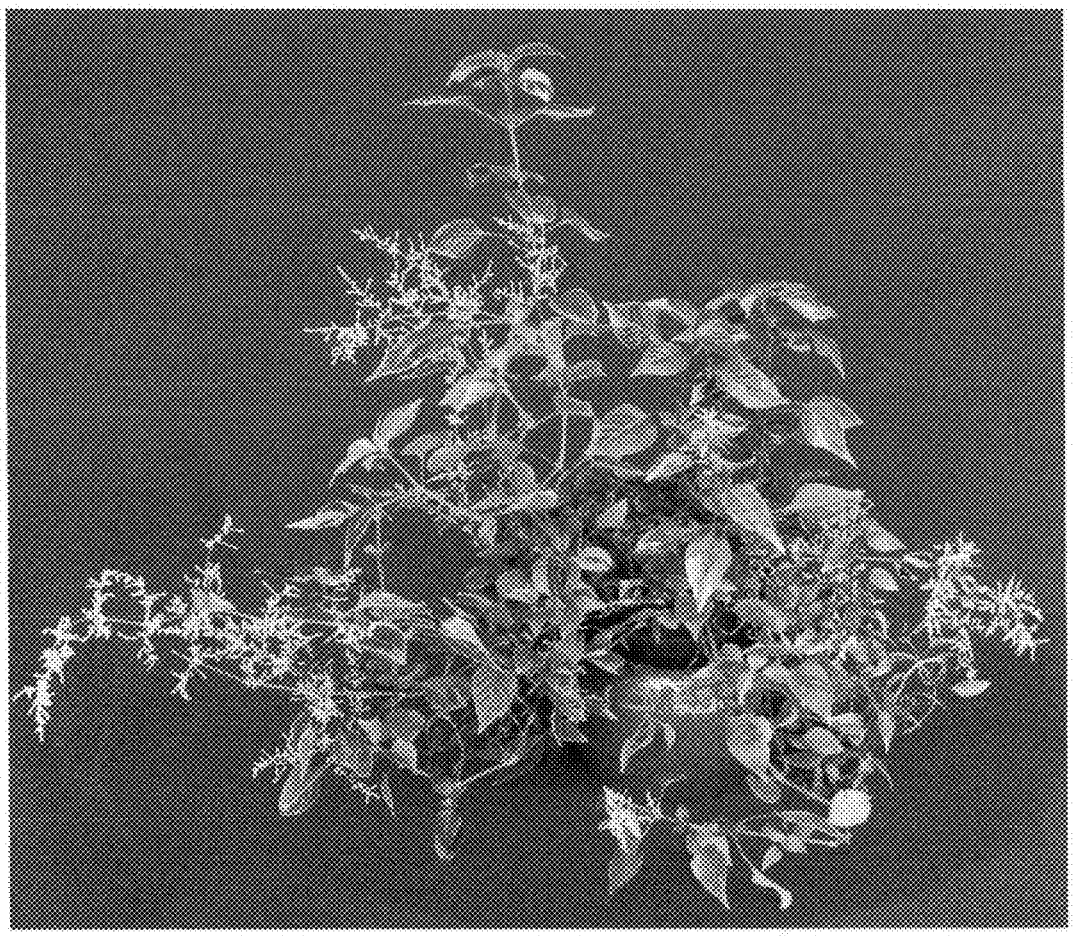

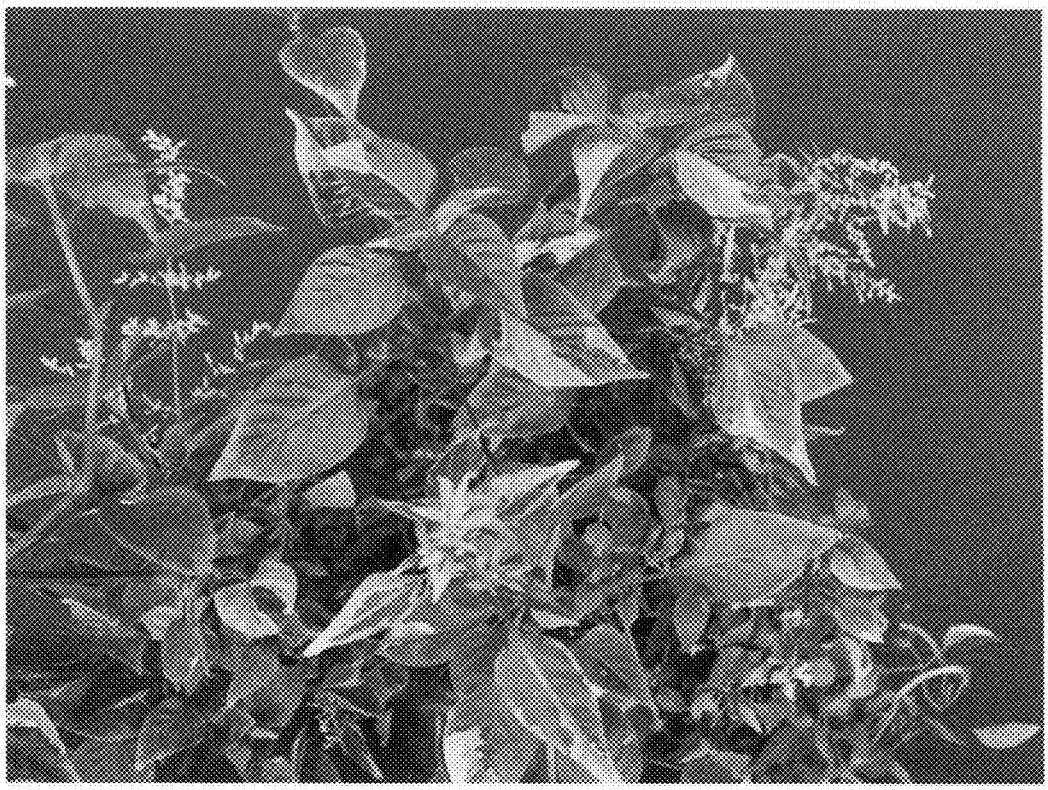

* * * * *